US012690935B2

(12) United States Patent
Sowards et al.

(10) Patent No.: US 12,690,935 B2
(45) Date of Patent: Jul. 28, 2026

(54) PORTAL-ESTABLISHING DEVICES AND METHODS THEREOF FOR ESTABLISHING PORTALS IN PROCEDURAL BARRIERS

(71) Applicant: Bard Access Systems, Inc., Salt Lake City, UT (US)

(72) Inventors: Steffan Sowards, Salt Lake City, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 1232 days.

(21) Appl. No.: 17/499,688

(22) Filed: Oct. 12, 2021

(65) Prior Publication Data

US 2022/0110707 A1 Apr. 14, 2022

Related U.S. Application Data

(60) Provisional application No. 63/091,185, filed on Oct. 13, 2020.

(51) Int. Cl.
| | |
|---|---|
| *A61B 46/10* | (2016.01) |
| *A61B 46/00* | (2016.01) |
| *A61B 46/20* | (2016.01) |

(52) U.S. Cl.
CPC .............. *A61B 46/10* (2016.02); *A61B 46/20* (2016.02); *A61B 46/40* (2016.02)

(58) Field of Classification Search
CPC ......... A61B 46/10; A61B 46/20; A61B 46/40; A61B 17/15; A61B 17/3421;
(Continued)

(56) References Cited

U.S. PATENT DOCUMENTS

| 2,831,174 A | 4/1958 | Hilmo |
|---|---|---|
| 2,959,766 A | 11/1960 | Edwin |

(Continued)

FOREIGN PATENT DOCUMENTS

| EP | 1318576 A1 | 6/2003 |
|---|---|---|
| EP | 3270817 A1 | 1/2018 |

(Continued)

OTHER PUBLICATIONS

PCT/US2019/015710 filed Jan. 29, 2019 International Preliminary Report on Patentability dated Apr. 29, 2019.
(Continued)

*Primary Examiner* — Camtu T Nguyen
(74) *Attorney, Agent, or Firm* — Rutan & Tucker LLP

(57) ABSTRACT

Disclosed herein are portal-establishing devices and methods thereof for establishing portals in procedural barriers. For example, a portal-establishing device includes a portal and a breaching mechanism. The portal includes a portal barrier in a protruding-end portion thereof. The portal is configured to enable one or more functional connections such as an optical connection or an electrical connection across a procedural barrier between a single-use medical device on a clinician-facing side of the procedural barrier and another medical device on a patient-facing side of the procedural barrier. The breaching mechanism is configured to breach the procedural barrier and place the portal over a breach in the procedural barrier. Methods of the portal-establishing devices include methods of using the portal-establishing devices.

14 Claims, 12 Drawing Sheets

(58) Field of Classification Search
CPC ..... A61B 17/3423; A61B 46/13; A61B 46/17;
A61B 46/23; A61M 2025/0266
See application file for complete search history.

(56) References Cited

U.S. PATENT DOCUMENTS

| | | |
|---|---|---|
| 3,329,928 A | 7/1967 | Broske |
| 3,532,095 A | 10/1970 | Miller et al. |
| 3,597,582 A | 8/1971 | Goode et al. |
| 3,605,743 A | 9/1971 | Arce |
| 3,649,952 A | 3/1972 | Harmon |
| 3,665,372 A | 5/1972 | Goode et al. |
| 3,673,548 A | 6/1972 | Mattingly, Jr. et al. |
| 3,746,814 A | 7/1973 | Lackey et al. |
| 3,824,556 A | 7/1974 | Berkovits et al. |
| 3,842,394 A | 10/1974 | Bolduc |
| 4,200,348 A | 4/1980 | Stupay |
| 4,220,387 A | 9/1980 | Biche et al. |
| 4,254,764 A | 3/1981 | Neward |
| 4,303,293 A | 12/1981 | Grunwald |
| 4,369,794 A | 1/1983 | Furler |
| 4,490,003 A | 12/1984 | Robinson |
| 4,614,395 A | 9/1986 | Peers-Trevarton |
| 4,632,121 A | 12/1986 | Johnson et al. |
| 4,700,997 A | 10/1987 | Strand |
| 4,702,256 A | 10/1987 | Robinson et al. |
| 4,761,143 A | 8/1988 | Owens et al. |
| 4,858,810 A | 8/1989 | Intlekofer et al. |
| 4,860,742 A | 8/1989 | Park et al. |
| 4,973,329 A | 11/1990 | Park et al. |
| 5,159,861 A | 11/1992 | Anderson |
| 5,178,159 A | 1/1993 | Christian |
| 5,217,435 A | 6/1993 | Kring |
| 5,325,746 A | 7/1994 | Anderson |
| 5,325,868 A | 7/1994 | Kimmelstiel |
| 5,334,045 A | 8/1994 | Cappa et al. |
| 5,354,326 A | 10/1994 | Comben et al. |
| 5,407,368 A | 4/1995 | Strand et al. |
| 5,423,877 A | 6/1995 | Mackey |
| 5,437,277 A | 8/1995 | Dumoulin et al. |
| 5,454,739 A | 10/1995 | Strand |
| 5,482,038 A | 1/1996 | Ruff |
| 5,489,225 A | 2/1996 | Julian |
| 5,501,675 A | 3/1996 | Erskine |
| 5,538,444 A | 7/1996 | Strand et al. |
| 5,560,358 A | 10/1996 | Arnold et al. |
| 5,591,119 A | 1/1997 | Adair |
| 5,624,281 A | 4/1997 | Christensson |
| 5,685,855 A | 11/1997 | Erskine |
| 5,752,915 A | 5/1998 | Neubauer et al. |
| 5,766,042 A | 6/1998 | Ries et al. |
| 5,769,786 A | 6/1998 | Wiegel |
| 5,792,045 A | 8/1998 | Adair |
| 5,797,880 A | 8/1998 | Erskine |
| 5,840,024 A | 11/1998 | Taniguchi et al. |
| 5,968,082 A | 10/1999 | Heil |
| 5,975,082 A | 11/1999 | Dowdy |
| 5,984,918 A | 11/1999 | Garito et al. |
| 6,050,976 A | 4/2000 | Thorne et al. |
| 6,090,052 A | 7/2000 | Akerfeldt et al. |
| 6,102,044 A | 8/2000 | Naidyhorski |
| 6,132,368 A | 10/2000 | Cooper |
| 6,140,722 A | 10/2000 | Ballard et al. |
| 6,162,101 A | 12/2000 | Fischer et al. |
| 6,319,015 B1 | 11/2001 | Faunce |
| 6,324,416 B1 | 11/2001 | Seibert |
| 6,330,480 B1 | 12/2001 | Van der Linden et al. |
| 6,350,160 B1 | 2/2002 | Feuersanger et al. |
| 6,415,168 B1 | 7/2002 | Putz |
| 6,428,336 B1 | 8/2002 | Akerfeldt |
| 6,546,270 B1 | 4/2003 | Goldin et al. |
| 6,620,136 B1 | 9/2003 | Pressly, Sr. et al. |
| 6,663,570 B2 | 12/2003 | Mott et al. |
| 6,673,078 B1 | 1/2004 | Muncie |
| 6,714,809 B2 | 3/2004 | Lee et al. |
| 6,780,065 B2 | 8/2004 | Schwarz |
| 6,799,991 B2 | 10/2004 | Williams et al. |
| 6,913,478 B2 | 7/2005 | Lamirey |
| 7,130,699 B2 | 10/2006 | Huff et al. |
| 7,144,378 B2 | 12/2006 | Arnott |
| 7,255,609 B1 | 8/2007 | Epstein |
| 7,274,956 B2 | 9/2007 | Mott et al. |
| 7,402,083 B2 | 7/2008 | Kast et al. |
| 7,452,360 B2 | 11/2008 | Trudeau et al. |
| 7,553,193 B2 | 6/2009 | Kast et al. |
| 7,585,118 B1 | 9/2009 | Lumpkin |
| 7,633,023 B1 | 12/2009 | Cappa et al. |
| 7,666,191 B2 | 2/2010 | Orban, III et al. |
| 7,753,696 B2 | 7/2010 | Hoecke et al. |
| 7,771,394 B2 | 8/2010 | Shue et al. |
| 7,819,844 B2 | 10/2010 | Spenser et al. |
| 7,972,282 B2 | 7/2011 | Clark et al. |
| 8,105,338 B2 | 1/2012 | Anderson et al. |
| 8,147,275 B1 | 4/2012 | Drake et al. |
| 8,206,175 B2 | 6/2012 | Boyd et al. |
| 8,267,873 B2 | 9/2012 | Yanuma |
| 8,388,541 B2 | 3/2013 | Messerly et al. |
| 8,480,427 B2 | 7/2013 | Marshalok |
| 8,548,601 B2 | 10/2013 | Chinn et al. |
| 8,597,042 B2 | 12/2013 | King |
| 8,603,011 B2 | 12/2013 | Landowski |
| 8,620,412 B2 | 12/2013 | Griffiths et al. |
| 8,639,340 B2 | 1/2014 | Sommer et al. |
| 8,666,510 B2 | 3/2014 | Chinn et al. |
| 8,781,555 B2 | 7/2014 | Burnside et al. |
| 8,849,382 B2 | 9/2014 | Cox et al. |
| 8,869,887 B2 | 10/2014 | Deere et al. |
| 8,932,258 B2 | 1/2015 | Blanchard et al. |
| 8,958,878 B2 | 2/2015 | Cejnar |
| 9,059,548 B2 | 6/2015 | Stump et al. |
| 9,095,680 B2 | 8/2015 | Steegers et al. |
| 9,101,775 B2 | 8/2015 | Barker |
| 9,107,594 B2 | 8/2015 | Selvitelli et al. |
| 9,108,027 B2 | 8/2015 | Eubanks et al. |
| 9,131,956 B2 | 9/2015 | Shaughnessy et al. |
| 9,144,395 B2 | 9/2015 | Sela et al. |
| 9,425,537 B2 | 8/2016 | Barker |
| 9,456,766 B2 | 10/2016 | Cox et al. |
| 9,492,097 B2 | 11/2016 | Wilkes et al. |
| 9,521,961 B2 | 12/2016 | Silverstein et al. |
| 9,526,440 B2 | 12/2016 | Burnside et al. |
| 9,549,685 B2 | 1/2017 | Cox et al. |
| 9,554,716 B2 | 1/2017 | Burnside et al. |
| 9,636,031 B2 | 5/2017 | Cox |
| 9,649,048 B2 | 5/2017 | Cox et al. |
| 9,656,093 B2 | 5/2017 | Villarta et al. |
| 9,662,506 B2 | 5/2017 | Govea |
| 9,675,784 B2 | 6/2017 | Belson |
| 9,681,823 B2 | 6/2017 | Messerly et al. |
| 9,808,647 B2 | 11/2017 | Rhodes et al. |
| 9,872,971 B2 | 1/2018 | Blanchard |
| 9,919,145 B2 | 3/2018 | Bondhus et al. |
| 9,950,139 B2 | 4/2018 | Blanchard et al. |
| 9,999,371 B2 | 6/2018 | Messerly et al. |
| 10,105,121 B2 | 10/2018 | Burnside et al. |
| 10,130,806 B2 | 11/2018 | Even et al. |
| 10,165,962 B2 | 1/2019 | Messerly et al. |
| 10,201,713 B2 | 2/2019 | Leven |
| 10,231,753 B2 | 3/2019 | Burnside et al. |
| 10,238,418 B2 | 3/2019 | Cox et al. |
| 10,238,880 B2 | 3/2019 | Thom et al. |
| 10,307,602 B2 | 6/2019 | Leven |
| 10,322,253 B2 | 6/2019 | Einav et al. |
| 10,342,575 B2 | 7/2019 | Cox et al. |
| 10,449,330 B2 | 10/2019 | Newman et al. |
| 10,524,691 B2 | 1/2020 | Newman et al. |
| 10,602,958 B2 | 3/2020 | Silverstein et al. |
| 10,751,509 B2 | 8/2020 | Misener |
| 10,772,696 B2 | 9/2020 | Thompson et al. |
| 10,849,695 B2 | 12/2020 | Cox et al. |
| 10,992,078 B2 | 4/2021 | Thompson et al. |
| D921,884 S | 6/2021 | Tran et al. |
| 11,246,674 B1 * | 2/2022 | Galbierz ............... A61G 10/02 |
| 11,474,310 B2 | 10/2022 | Sowards et al. |

(56)            References Cited

U.S. PATENT DOCUMENTS

| | | |
|---|---|---|
| 11,936,132 B2 | 3/2024 | Thompson et al. |
| 2002/0197905 A1 | 12/2002 | Kaufmann et al. |
| 2003/0199827 A1 | 10/2003 | Thorne |
| 2003/0216723 A1 | 11/2003 | Shinmura et al. |
| 2004/0039372 A1 | 2/2004 | Carmody |
| 2004/0146252 A1 | 7/2004 | Healy et al. |
| 2005/0177199 A1 | 8/2005 | Hansen et al. |
| 2005/0283216 A1 | 12/2005 | Pyles |
| 2006/0025677 A1 | 2/2006 | Verard et al. |
| 2006/0030864 A1 | 2/2006 | Kennedy, et al. |
| 2006/0161138 A1 | 7/2006 | Orban et al. |
| 2006/0173407 A1 | 8/2006 | Shaughnessy et al. |
| 2007/0062544 A1 | 3/2007 | Rauk Bergstrom et al. |
| 2007/0118079 A1 | 5/2007 | Moberg et al. |
| 2007/0160327 A1 | 7/2007 | Lewallen et al. |
| 2007/0161969 A1 | 7/2007 | Andersen |
| 2007/0293719 A1 | 12/2007 | Scopton et al. |
| 2008/0009720 A1 | 1/2008 | Schefelker et al. |
| 2008/0046062 A1 | 2/2008 | Camps et al. |
| 2008/0177361 A1 | 7/2008 | Anderson |
| 2008/0236598 A1 | 10/2008 | Gobel |
| 2008/0287876 A1 | 11/2008 | Shue et al. |
| 2008/0304793 A1 | 12/2008 | Benaron et al. |
| 2009/0156926 A1 | 6/2009 | Messerly et al. |
| 2009/0234328 A1* | 9/2009 | Cox .................... A61B 5/06 |
| | | 600/509 |
| 2010/0036227 A1 | 2/2010 | Cox et al. |
| 2010/0049126 A1 | 2/2010 | Bronfeld et al. |
| 2010/0139669 A1 | 6/2010 | Piferi et al. |
| 2010/0204569 A1 | 8/2010 | Burnside et al. |
| 2010/0300459 A1* | 12/2010 | Lair .................... A61B 46/00 |
| | | 128/853 |
| 2011/0160824 A1 | 6/2011 | Ware et al. |
| 2011/0166528 A1 | 7/2011 | Millerd et al. |
| 2011/0250775 A1 | 10/2011 | Bies et al. |
| 2011/0257503 A1 | 10/2011 | Mehdizadeh et al. |
| 2012/0071752 A1 | 3/2012 | Sewell et al. |
| 2012/0253320 A1 | 10/2012 | Steegers et al. |
| 2013/0023729 A1 | 1/2013 | Vazales et al. |
| 2013/0095689 A1 | 4/2013 | Hayman et al. |
| 2013/0104884 A1 | 5/2013 | Vazales et al. |
| 2013/0109980 A1 | 5/2013 | Teo |
| 2013/0211225 A1 | 8/2013 | Zhang |
| 2013/0245640 A1 | 9/2013 | Whitmore, III |
| 2013/0247921 A1 | 9/2013 | Dye et al. |
| 2013/0269713 A1 | 10/2013 | Bui et al. |
| 2013/0289417 A1 | 10/2013 | Grunwald et al. |
| 2013/0308137 A1 | 11/2013 | Manzke et al. |
| 2013/0317356 A1 | 11/2013 | Ramachandran et al. |
| 2013/0331688 A1 | 12/2013 | Heigl et al. |
| 2013/0337674 A1 | 12/2013 | Stump et al. |
| 2014/0150782 A1 | 6/2014 | Vazales et al. |
| 2015/0012072 A1 | 1/2015 | Johnson et al. |
| 2015/0031987 A1 | 1/2015 | Pameijer et al. |
| 2015/0105654 A1 | 4/2015 | Meyer |
| 2015/0144514 A1 | 5/2015 | Brennan et al. |
| 2015/0148615 A1 | 5/2015 | Brennan et al. |
| 2015/0164583 A1 | 6/2015 | Zarins et al. |
| 2015/0177467 A1 | 6/2015 | Gniadek et al. |
| 2015/0190615 A1 | 7/2015 | Shaltis |
| 2015/0223897 A1 | 8/2015 | Kostrzewski et al. |
| 2015/0305816 A1 | 10/2015 | Hadzic |
| 2016/0018602 A1 | 1/2016 | Govari et al. |
| 2016/0158499 A1* | 6/2016 | Helm .................... A61M 39/18 |
| | | 604/180 |
| 2016/0213432 A1 | 7/2016 | Flexman et al. |
| 2017/0014194 A1 | 1/2017 | Duindam et al. |
| 2017/0181646 A1 | 6/2017 | Hayes et al. |
| 2017/0231700 A1 | 8/2017 | Cox et al. |
| 2017/0261699 A1 | 9/2017 | Compton et al. |
| 2017/0296284 A1 | 10/2017 | Turturro et al. |
| 2017/0333136 A1 | 11/2017 | Hladio et al. |
| 2018/0071509 A1 | 3/2018 | Tran et al. |
| 2018/0110951 A2 | 4/2018 | Beard |
| 2018/0140170 A1 | 5/2018 | Van Putten et al. |
| 2018/0289927 A1 | 10/2018 | Messerly |
| 2019/0069877 A1 | 3/2019 | Burnside et al. |
| 2019/0180647 A1 | 6/2019 | Fujiki |
| 2019/0231172 A1 | 8/2019 | Barron et al. |
| 2019/0237902 A1 | 8/2019 | Thompson et al. |
| 2019/0350621 A1 | 11/2019 | Zitnick et al. |
| 2019/0350663 A1 | 11/2019 | Thompson et al. |
| 2020/0221934 A1 | 7/2020 | Van Der Mark et al. |
| 2020/0330173 A1 | 10/2020 | Kapadia et al. |
| 2020/0345441 A1 | 11/2020 | Thompson et al. |
| 2021/0030504 A1 | 2/2021 | Thompson et al. |
| 2021/0038322 A1 | 2/2021 | Thompson et al. |
| 2021/0298680 A1 | 9/2021 | Sowards et al. |
| 2021/0307856 A1 | 10/2021 | Aguirre |
| 2022/0110708 A1 | 4/2022 | Misener et al. |
| 2022/0128770 A1 | 4/2022 | Sowards et al. |
| 2022/0241044 A1 | 8/2022 | Thompson et al. |
| 2023/0248459 A1 | 8/2023 | Thompson et al. |
| 2023/0390015 A1 | 12/2023 | Thompson et al. |
| 2024/0170887 A1 | 5/2024 | Thompson et al. |
| 2024/0350206 A1 | 10/2024 | Thompson et al. |
| 2024/0366330 A1 | 11/2024 | Thompson et al. |
| 2025/0192473 A1 | 6/2025 | Thompson et al. |

FOREIGN PATENT DOCUMENTS

| | | |
|---|---|---|
| EP | 3673801 A1 | 7/2020 |
| WO | 9413201 A1 | 6/1994 |
| WO | 9619017 A1 | 6/1996 |
| WO | 9822180 A1 | 5/1998 |
| WO | 2004101068 A1 | 11/2004 |
| WO | 2005016451 A1 | 2/2005 |
| WO | 2005044332 A2 | 5/2005 |
| WO | 2005072807 A1 | 8/2005 |
| WO | 2005077453 A2 | 8/2005 |
| WO | 2007058816 A2 | 5/2007 |
| WO | 2007109285 A2 | 9/2007 |
| WO | 2007149618 A2 | 12/2007 |
| WO | 2009050599 A2 | 4/2009 |
| WO | 2010123701 A1 | 10/2010 |
| WO | 2011033107 A1 | 3/2011 |
| WO | 2011082160 A2 | 7/2011 |
| WO | 2012102745 A2 | 8/2012 |
| WO | 2015075002 A1 | 5/2015 |
| WO | 2016/146993 A1 | 9/2016 |
| WO | 2019/148201 A1 | 8/2019 |
| WO | 2019/165011 A1 | 8/2019 |
| WO | 2019/221926 A1 | 11/2019 |
| WO | 2021021408 A1 | 2/2021 |
| WO | 2021026502 A1 | 2/2021 |
| WO | 2022/081583 A1 | 4/2022 |
| WO | 2022081591 A1 | 4/2022 |
| WO | 2022/093991 A1 | 5/2022 |

OTHER PUBLICATIONS

PCT/US2019/015710 filed Jan. 29, 2019 International Search Report and Written Opinion dated Apr. 29, 2019.

PCT/US2019/018851 filed Feb. 20, 2019 Internation Search Report and Written Opinion dated May 7, 2019.

PCT/US2019/018851 filed Feb. 20, 2019 International Preliminary Report on Patentability dated May 7, 2019.

PCT/US2020/41267 filed Jul. 8, 2020 Internation Search Report and Written Opinion dated Oct. 1, 2020.

PCT/US2020/45498 filed Aug. 7, 2020 International Search Report and Written Opinion dated Oct. 4, 2020.

U.S. Appl. No. 12/426,175, filed Apr. 17, 2009 Advisory Action dated Nov. 26, 2013.

U.S. Appl. No. 12/426,175, filed Apr. 17, 2009 Decision on Appeal dated Nov. 7, 2016.

U.S. Appl. No. 12/426,175, filed Apr. 17, 2009 Examiner's Answer dated Oct. 7, 2014.

U.S. Appl. No. 12/426,175, filed Apr. 17, 2009 Final Office Action dated Aug. 2, 2013.

U.S. Appl. No. 12/426,175, filed Apr. 17, 2009 Final Office Action dated Jan. 31, 2014.

(56)     References Cited

OTHER PUBLICATIONS

U.S. Appl. No. 12/426,175, filed Apr. 17, 2009 Non-Final Office Action dated Dec. 3, 2012.
U.S. Appl. No. 12/426,175, filed Apr. 17, 2009 Notice of Allowance dated Dec. 13, 2016.
U.S. Appl. No. 12/715,556, filed Mar. 2, 2010 Final Office Action dated Oct. 2, 2013.
U.S. Appl. No. 12/715,556, filed Mar. 2, 2010 Non-Final Office Action dated Sep. 13, 2012.
U.S. Appl. No. 15/585,051, filed May 2, 2017 Examiner's Answer dated May 2, 2019.
U.S. Appl. No. 15/585,051, filed May 2, 2017 Final Office Action dated Feb. 28, 2018.
U.S. Appl. No. 15/585,051, filed May 2, 2017 Final Office Action dated Mar. 15, 2018.
U.S. Appl. No. 15/585,051, filed May 2, 2017 Non-Final Office Action dated Jul. 14, 2017.
U.S. Appl. No. 16/261,368, filed Jan. 29, 2019 Advisory Action dated Jul. 21, 2020.
U.S. Appl. No. 16/261,368, filed Jan. 29, 2019 Non-Final Office Action dated Jan. 23, 2020.
U.S. Appl. No. 16/261,368, filed Jan. 29, 2019 Notice of Allowance dated Jan. 15, 2021.
U.S. Appl. No. 16/281,079, filed Feb. 20, 2019 Final Office Action dated Aug. 25, 2020.
U.S. Appl. No. 16/281,079, filed Feb. 20, 2019 Non-Final Office Action dated Apr. 1, 2020.
U.S. Appl. No. 16/281,079, filed Feb. 20, 2019 Non-Final Office Action dated Apr. 20, 2021.
U.S. Appl. No. 16/402,074, filed May 2, 2019 Non-Final Office Action dated Apr. 16, 2020.
U.S. Appl. No. 16/932,425, filed Jul. 17, 2020 Non-Final Office Action dated Jun. 18, 2021.
U.S. Appl. No. 16/932,425, filed Jul. 17, 2020 Notice of Allowance dated Jan. 10, 2022.
Design U.S. Appl. No. 29/658,136 Specification and Drawings filed Jul. 27, 2018.
U.S. Appl. No. 17/499,635, filed Oct. 12, 2021 Non-Final Office Action dated Dec. 4, 2024.
U.S. Appl. No. 17/499,635, filed Oct. 12, 2021 Restriction Requirement dated Jun. 12, 2024.
U.S. Appl. No. 17/512,501, filed Oct. 27, 2021 Examiner's Answer dated Jun. 18, 2024.
U.S. Appl. No. 18/135,330, filed Apr. 17, 2023, Non-Final Office Action dated Jul. 15, 2024.
U.S. Appl. No. 18/539,518, filed Dec. 14, 2023, Non-Final Office Action dated Jun. 21, 2024.
U.S. Appl. No. 18/539,518, filed Dec. 14, 2023, Notice of Allowance dated Nov. 7, 2024.
PCT/US2021/054593 filed Oct. 12, 2021 International Search Report and Written Opinion dated Jan. 24, 2022.
PCT/US2021/054607 filed Oct. 12, 2021 International Search Report and Written Opinion dated Jan. 21, 2022.
U.S. Appl. No. 16/281,079, filed Feb. 20, 2019 Examiner's Answer dated Feb. 25, 2022.
EP 20849119.1 filed Mar. 4, 2022 Extended European Search Report dated Jun. 26, 2023.

U.S. Appl. No. 16/281,079, filed Feb. 20, 2019 Board Decision dated Jun. 6, 2023.
U.S. Appl. No. 16/988,452, filed Aug. 7, 2020 Advisory Action dated Oct. 2, 2023.
U.S. Appl. No. 16/988,452, filed Aug. 7, 2020 Final Office Action dated Mar. 16, 2023.
U.S. Appl. No. 16/988,452, filed Aug. 7, 2020 Non-Final Office Action dated Nov. 9, 2023.
U.S. Appl. No. 17/240,826, filed Apr. 26, 2021 Notice of Allowance dated Nov. 9, 2023.
U.S. Appl. No. 17/240,826, filed Apr. 26, 2021, Non-Final Office Action dated Jul. 19, 2023.
U.S. Appl. No. 17/512,501, filed Oct. 27, 2021 Final Office Action dated Aug. 31, 2023.
PCT/US19/30470 filed May 2, 2019 International Search Report and Written Opinion dated Jul. 19, 2019.
U.S. Appl. No. 16/923,912, filed Jul. 8, 2020 Notice of Allowance dated Mar. 27, 2023.
U.S. Appl. No. 16/988,452, filed Aug. 7, 2020 Non-Final Office Action dated Mar. 16, 2023.
U.S. Appl. No. 17/512,501, filed Oct. 27, 2021 Non-Final Office Action dated Feb. 17, 2023.
U.S. Appl. No. 17/512,501, filed Oct. 27, 2021 Restriction Requirement dated Sep. 30, 2022.
U.S. Appl. No. 17/723,246, filed Apr. 18, 2022, Non-Final Office Action dated Sep. 27, 2022.
U.S. Appl. No. 17/723,246, filed Apr. 18, 2022, Notice of Allowance dated Jan. 27, 2023.
U.S. Appl. No. 16/988,452, filed Aug. 7, 2020 Notice of Allowance dated Feb. 29, 2024.
U.S. Appl. No. 18/135,330, filed Apr. 17, 2023, Non-Final Office Action dated Dec. 18, 2023.
U.S. Appl. No. 18/235,334, filed Aug. 17, 2023, Notice of Allowance dated Apr. 4, 2024.
"Sampling Accessories" Spectrometers Accessories Catalogue, pp. 71-102, XP055014465, retrieved from the Internet URL: http//www.mikropack.de/d/specto/pdfy-downoads/sampling accessories. pdf, Jan. 1, 2004 (Jan. 1, 2004).
PCT/US2021/056896 filed Oct. 27, 2021 International Search Report and Written Opinion dated Mar. 22, 2022.
U.S. Appl. No. 17/499,635, filed Oct. 12, 2021 Advisory Action dated Aug. 8, 2025.
U.S. Appl. No. 17/499,635, filed Oct. 12, 2021 Final Office Action dated May 19, 2025.
U.S. Appl. No. 17/499,635, filed Oct. 12, 2021 Non-Final Office Action dated Aug. 21, 2025.
U.S. Appl. No. 17/512,501, filed Oct. 27, 2021 Board Decision dated Jul. 25, 2025.
U.S. Appl. No. 18/135,330, filed Apr. 17, 2023, Notice of Allowance dated Dec. 18, 2024.
U.S. Appl. No. 18/761,182, filed Jul. 1, 2024 Non-Final Office Action dated Jun. 20, 2025.
U.S. Appl. No. 18/761,182, filed Jul. 1, 2024 Notice of Allowance dated Oct. 23, 2025.
U.S. Appl. No. 18/773,870, filed Jul. 16, 2024 Non-Final Office Action dated Sep. 23, 2025.

* cited by examiner

PORTAL-ESTABLISHING DEVICES AND METHODS THEREOF FOR ESTABLISHING PORTALS IN PROCEDURAL BARRIERS

PRIORITY

This application claims the benefit of priority to U.S. Provisional Application No. 63/091,185, filed Oct. 13, 2020, which is incorporated by reference in its entirety into this application.

BACKGROUND

Procedural fields are typically established about patients with one or more procedural barriers before medical procedures. For example, sterile fields can be established over or around patients by covering the patients with sterile drapes. Oftentimes, the medical procedures require multiple-use medical devices that cannot be sterilized, which mandate placement of such medical devices under the sterile drapes; however, sterile single-use medical devices often need to be functionally connected to the multiple-use medical devices. Some existing solutions rely on breaching sterile drapes to make functional connections between sterile single-use medical devices and multiple-use medical devices. But arbitrarily breaching such sterile drapes risks contaminating the sterile fields carefully established about the patients. That, and establishing some functional connections such as optical connections between the sterile single-use medical devices and the multiple-use medical devices can be difficult, particularly through arbitrary, self-made breaches in the sterile drapes. What is needed are procedural barriers with medical device-connecting portals that facilitate establishing safe, routine, functional connections between sterile single-use medical devices and other medical devices such as multiple-use medical devices.

Disclosed herein are portal-establishing devices and methods thereof for establishing portals in procedural barriers.

SUMMARY

Disclosed herein is a portal-establishing device including, in some embodiments, a portal and a breaching mechanism. The portal includes a portal barrier in a protruding-end portion thereof. The portal is configured to enable one or more functional connections across a procedural barrier between a single-use medical device on a clinician-facing side of the procedural barrier and another medical device on a patient-facing side of the procedural barrier. The breaching mechanism is configured to breach the procedural barrier and place the portal over a breach in the procedural barrier.

In some embodiments, the portal barrier is a transparent sheet of polymeric material. The sheet has sufficient optical transmissibility for establishing an optical connection across the sheet for the one-or-more functional connections between the single-use medical device and the other medical device.

In some embodiments, the sheet is sufficiently tear resistant for establishing an electrical connection across the sheet for the one-or-more functional connections between the single-use medical device and the other medical device without propagating any hole or tear made in the sheet of polymeric material to effectuate the electrical connection.

In some embodiments, the portal barrier is a split septum for establishing an optical connection, an electrical connection, or both the optical connection and the electrical connection across the septum for the one-or-more functional connections between the single-use medical device and the other medical device.

In some embodiments, the breaching mechanism includes an extension of the portal having internal threads configured to screw together with a protruding portion of the other medical device having external threads. The extension of the portal is configured to breach the procedural barrier with an internal cutting edge when screwed together with the protruding portion of the other medical device with the procedural barrier therebetween.

In some embodiments, the breaching mechanism includes an extension of the portal having one or more internal magnetic elements configured to couple with one or more external magnetic elements of a protruding portion of the other medical device. The extension of the portal is configured to breach the procedural barrier with an internal cutting edge when coupled together with the protruding portion of the other medical device with the procedural barrier therebetween.

In some embodiments, the breaching mechanism includes an extension of the portal having external threads configured to screw together with a protruding portion of the other medical device having internal threads. The extension of the portal is configured to breach the procedural barrier with an external cutting edge when screwed together with the protruding portion of the other medical device with the procedural barrier therebetween.

In some embodiments, the breaching mechanism includes a cap coupled by a hinge pin to a rigid band configured to sit over a protruding portion of the other medical device with the procedural barrier therebetween. The cap is configured to breach the procedural barrier with a cutting edge when closed over the band.

In some embodiments, the portal extends from the cap along a centerline of the cap such that the portal barrier is aligned with the breach in the procedural barrier when the procedural barrier is breached by the cap.

In some embodiments, the breaching mechanism includes a cap configured to sit over a protruding portion of the other medical device with the procedural barrier therebetween. An extension arm coupled by a hinge pin to the cap is configured to breach the procedural barrier with a punch of the extension arm when the punch is pushed through the procedural barrier by articulating the extension arm.

In some embodiments, the portal extends from the extension arm along a centerline of the punch but opposite thereof such that the portal barrier is aligned with the breach in the procedural barrier when the procedural barrier is breached by the punch.

In some embodiments, the breaching mechanism includes a rigid band configured to sit over a protruding portion of the other medical device with the procedural barrier therebetween. A cap coupled by a hinge pin to the band is configured to breach the procedural barrier with a punch of the cap when the punch is pushed through the procedural barrier with by way of articulating the cap.

In some embodiments, the portal extends from the cap along a centerline of the punch but opposite thereof such that the portal barrier is aligned with the breach in the procedural barrier when the procedural barrier is breached by the punch.

In some embodiments, the portal-establishing device is sterile and the procedural barrier is a sterile drape.

Also disclosed herein is a method of a portal-establishing device. The method includes a procedural barrier-breaching step and a portal-placing step. The procedural barrier-breaching step includes breaching a procedural barrier between a single-use medical device on a clinician-facing side of the procedural barrier and another medical device on a patient-facing side of the procedural barrier with a breaching mechanism of the portal-establishing device. The portal-placing step includes placing a portal over a breach in the procedural barrier. The portal-placing step enables one or more functional connections between the single-use medical device and the other medical device through the portal of the portal-establishing device.

In some embodiments, the method further includes a functional connection-establishing step. The functional connection-establishing step includes establishing an optical connection for the one-or-more functional connections across a transparent sheet of polymeric material having sufficient optical transmissibility for the optical connection as the portal barrier.

In some embodiments, the functional connection-establishing step includes establishing an electrical connection for the one-or-more functional connections across the sheet. The sheet has sufficient tear resistance for the functional connection-establishing step when establishing the electrical connection without propagating any hole or tear made in the sheet to effectuate the electrical connection.

In some embodiments, the method further includes a functional connection-establishing step. The functional connection-establishing step includes establishing an optical connection, an electrical connection, or both the optical connection and the electrical connection for the one-or-more functional connections across a split septum as the portal barrier.

In some embodiments, the method further includes a device-mating step. The device-mating step includes screwing together an extension of the portal having internal threads and a protruding portion of the other medical device having external threads. The procedural barrier-breaching step further includes breaching the procedural barrier between the extension of the portal and the protruding portion of the other medical device with an internal cutting edge of the extension of the portal while performing the device-mating step.

In some embodiments, the method further includes a device-mating step. The device-mating step includes magnetically coupling together an extension of the portal having one or more internal magnetic elements and a protruding portion of the other medical device having one or more external magnetic elements. The procedural barrier-breaching step further includes breaching the procedural barrier between the extension of the portal and the protruding portion of the other medical device with an internal cutting edge of the extension of the portal while performing the device-mating step.

In some embodiments, the method further includes a device-mating step. The device-mating step includes screwing together an extension of the portal having external threads and a protruding portion of the other medical device having internal threads. The procedural barrier-breaching step further includes breaching the procedural barrier between the extension of the portal and the protruding portion of the other medical device with an external cutting edge of the extension of the portal while performing the device-mating step.

In some embodiments, the procedural barrier-breaching step further includes closing a cap coupled by a hinge pin to a rigid band over a protruding portion of the other medical device. In addition, the procedural barrier-breaching step includes breaching the procedural barrier between the cap and the protruding portion of the other medical device with a cutting edge of the cap while closing the cap over the protruding portion of the other medical device.

In some embodiments, the procedural barrier-breaching step further includes articulating an extension arm coupled by a hinge pin to a cap over a protruding portion of the other medical device. In addition, the procedural barrier-breaching step includes breaching the procedural barrier between the cap and the protruding portion of the other medical device by pushing a punch of the extension arm through the procedural barrier while articulating the extension arm.

In some embodiments, the procedural barrier-breaching step further includes articulating a cap coupled by a hinge pin to a rigid band over a protruding portion of the other medical device. In addition, the procedural barrier-breaching step includes breaching the procedural barrier between the cap and the protruding portion of the other medical device by pushing a punch of the cap through the procedural barrier while articulating the cap.

In some embodiments, the portal-establishing device is sterile and the procedural barrier is a sterile drape.

Also disclosed herein is a procedural barrier including, in some embodiments, a portal integrated into the procedural barrier. The portal includes a portal barrier in a protruding-end portion thereof configured to enable one or more functional connections across the procedural barrier between a single-use medical device on a clinician-facing side of the procedural barrier and another medical device on a patient-facing side of the procedural barrier.

These and other features of the concepts provided herein will become more apparent to those of skill in the art in view of the accompanying drawings and following description, which describe particular embodiments of such concepts in greater detail.

DRAWINGS

DESCRIPTION

Figure 1:
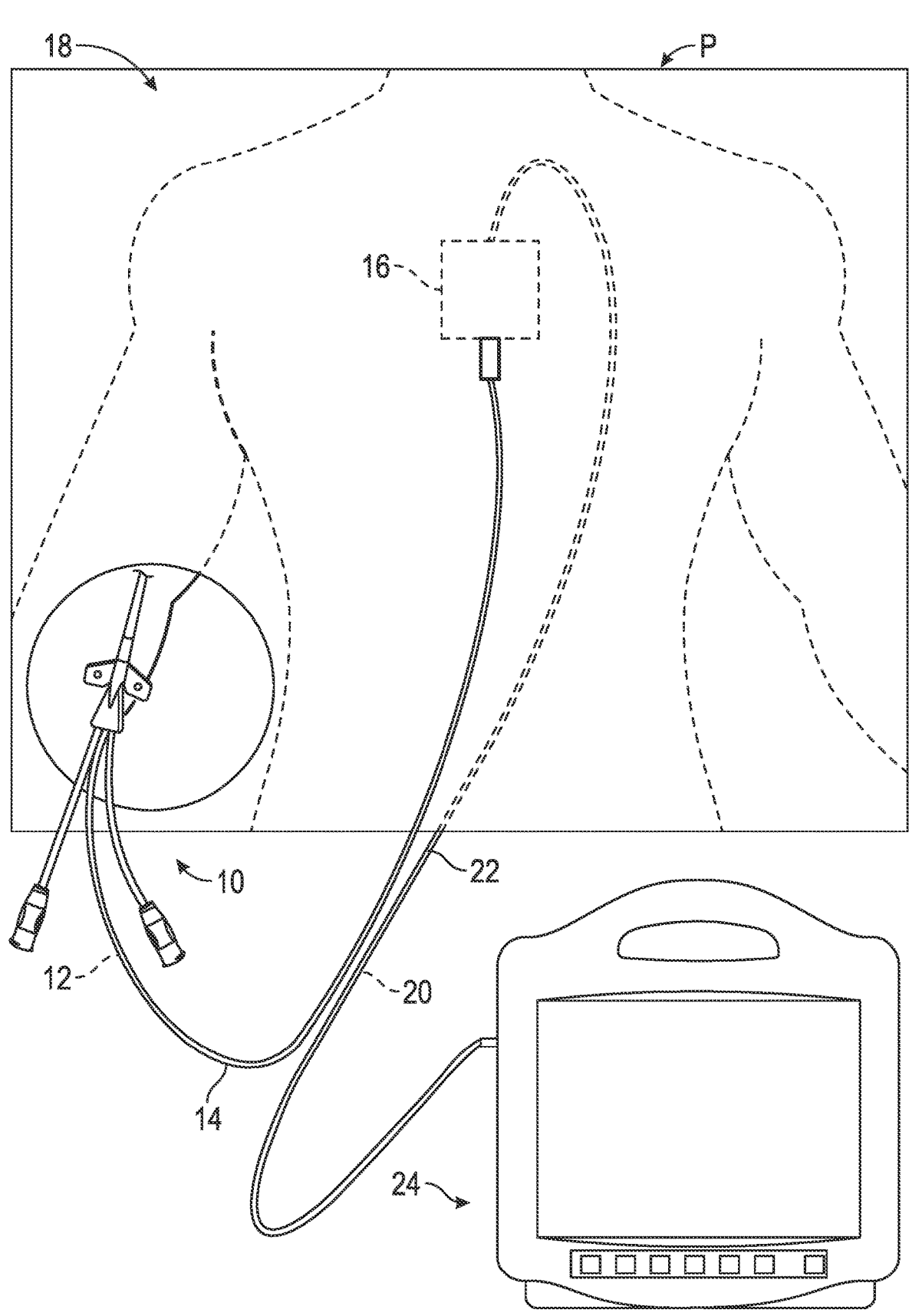
FIG. 1 illustrates functionally connected single-use and multiple-use medical devices of an optical shape-sensing system in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

FIG. 1 illustrates functionally connected single-use and multiple-use medical devices of an optical shape-sensing system in accordance with some embodiments.

As set forth above, medical procedures often require multiple-use medical devices that cannot be sterilized, which mandate placement of such medical devices under sterile drapes; however, sterile single-use medical devices often need to be functionally connected to the multiple-use medical devices. Indeed, as shown, the optical shape-sensing system includes a single-use peripherally inserted central catheter ("PICC") 10 having an optical-fiber stylet 12 disposed in an extension tube 14 functionally connected to a relay module 16 over a patient P but under a sterile drape 18 outside of a sterile field. The relay module 16, in turn, includes an optical fiber 20 disposed in a patch cable 22 functionally connected to a console 24 or an optical interrogator thereof that is also outside of the sterile field. Again, some existing solutions rely on breaching sterile drapes (e.g., the sterile drape 18) to make functional connections between sterile single-use medical devices (e.g., the PICC 10) and multiple-use medical devices (e.g., the relay module 16, the console 24, etc.). But arbitrarily breaching such sterile drapes risks contaminating the sterile fields carefully established about the patients. That, and establishing some functional connections such as optical connections between the sterile single-use medical devices and the multiple-use medical devices can be difficult, particularly through arbitrary, self-made breaches in the sterile drapes. What is needed are procedural barriers with medical device-connecting portals that facilitate establishing safe, routine, functional connections between sterile single-use medical devices and other medical devices such as multiple-use medical devices.

Disclosed herein are portal-establishing devices and methods thereof for establishing portals in procedural barriers.

Portal-Establishing Devices

Each portal-establishing device of those disclosed herein includes a portal and a breaching mechanism. Description for portals is set forth immediately below. Description for the breaching mechanisms is set forth thereafter in the context of one or more of the portal-establishing devices.

Figure 2:
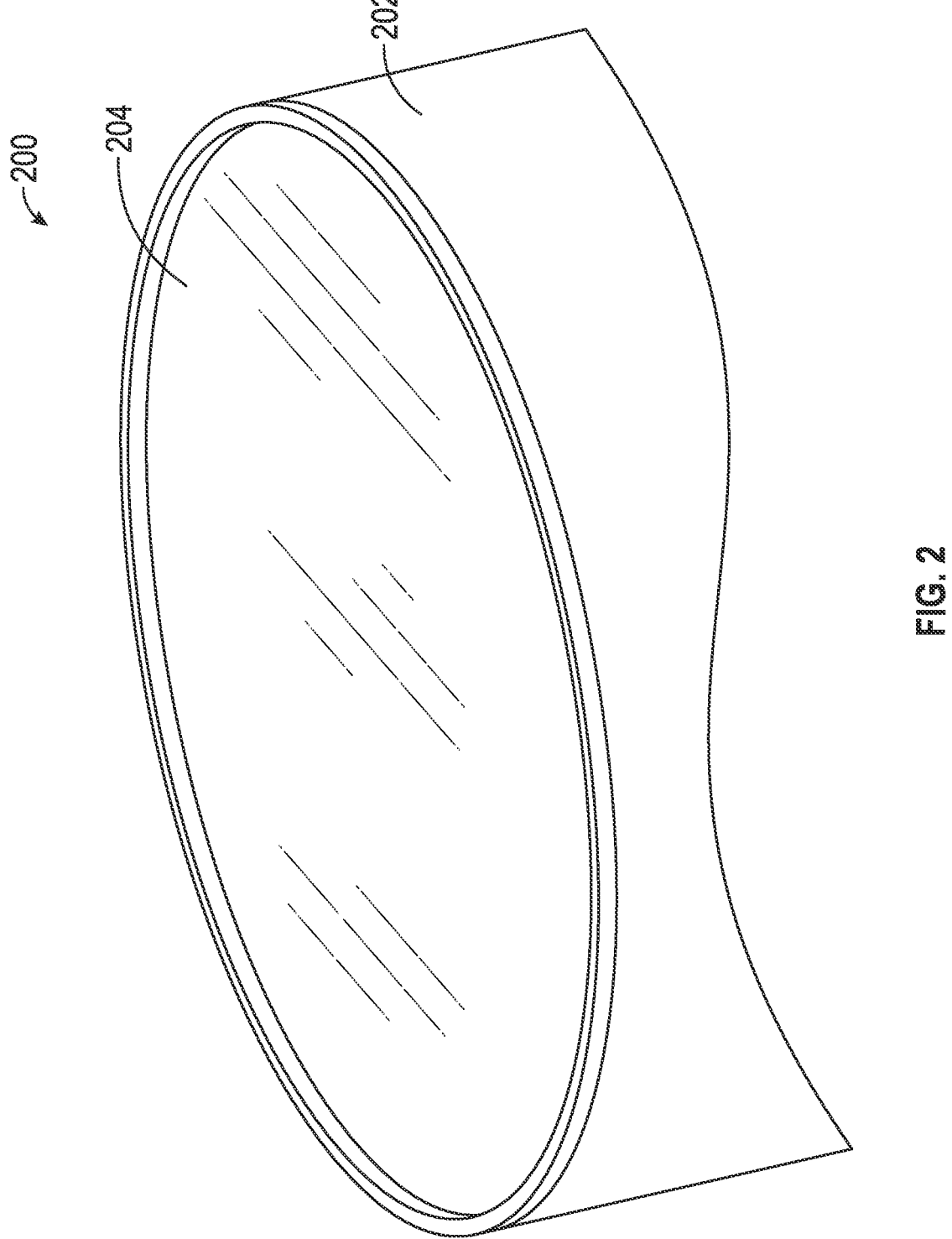
FIG. 2 illustrates a portal having a portal barrier of a transparent sheet of polymeric material in accordance with some embodiments.
Figure 3:
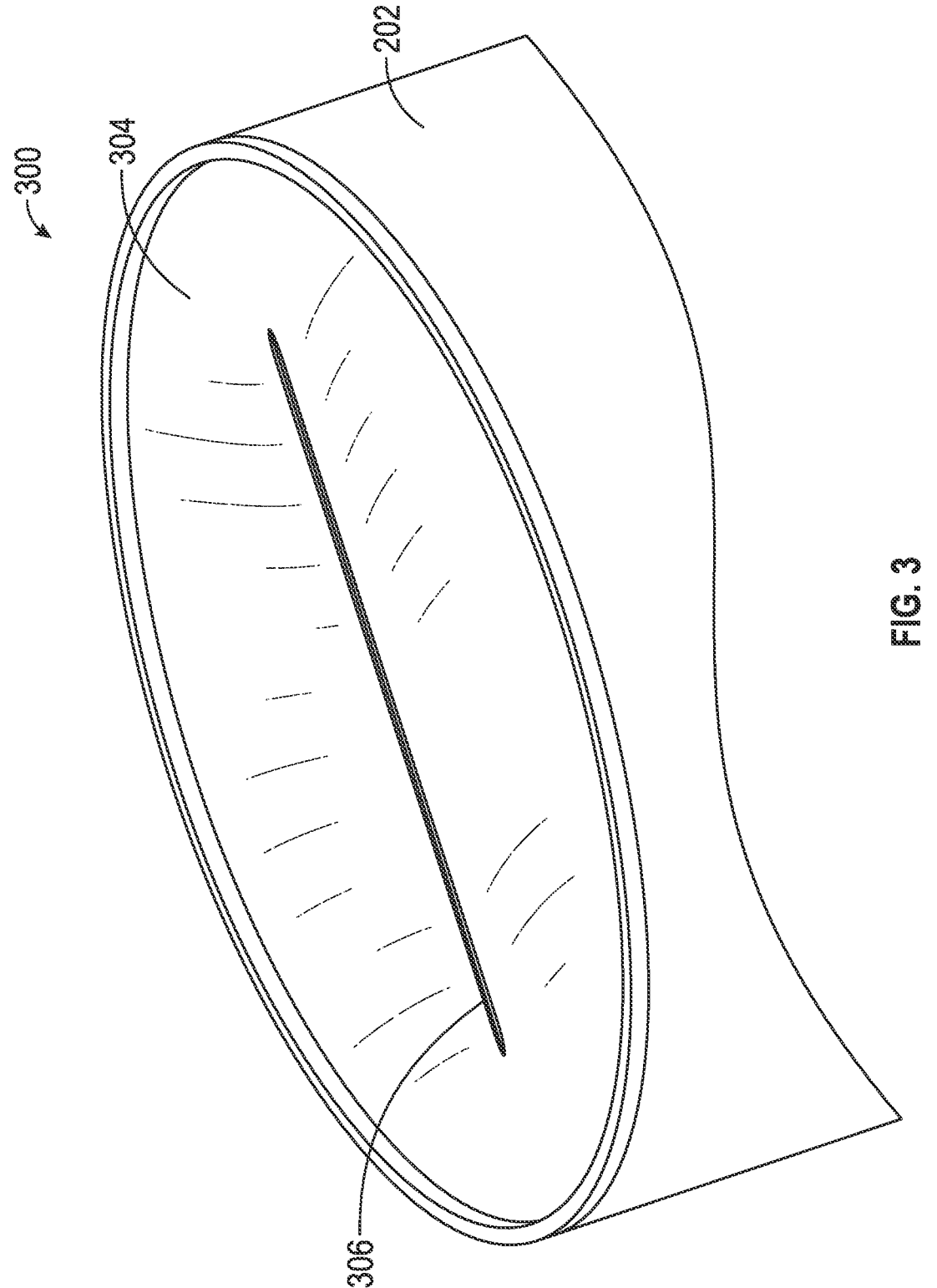
FIG. 3 illustrates a portal having a portal barrier of a splittable septum in accordance with some embodiments.

FIGS. 2 and 3 illustrate alternative portals 200 and 300 of the portal-establishing devices in accordance with some embodiments.

As shown, the portal 200 or 300 is a conduit 202 (e.g., a hollow right cylinder) including a portal barrier 204 or 304 in a protruding-end portion of the portal 200 or 300 or the conduit 202 thereof that protrudes from a portal-establishing device. The portal 200 or 300 is configured to enable one or more functional connections (e.g., an optical connection, an electrical connection, etc.) across a procedural barrier (e.g., the sterile barrier 18) between a single-use medical device (e.g., the PICC 10) on a clinician-facing side of the procedural barrier and another medical device such as a multiple-use medical device (e.g., the relay 16, the console 24, etc.) on a patient-facing side of the procedural barrier.

FIG. 2 illustrates the portal 200 having the portal barrier 204 of a transparent sheet of polymeric material in accordance with some embodiments.

The portal barrier 204 is a transparent sheet of polymeric material such as a single non-laminated sheet of polymeric material or two-or-more layers of polymeric material laminated together in a laminated sheet. The sheet can have sufficient optical transmissibility for establishing an optical connection across the sheet for the one-or-more functional connections between the single-use medical device and the multiple-use medical device. The sheet can be sufficiently tear resistant for establishing an electrical connection across the sheet for the one-or-more functional connections between the single-use medical device and the multiple-use medical device without propagating any hole or tear made in the sheet of polymeric material to effectuate the electrical connection. The polymeric material of the sheet can be a polyethylene, a polypropylene, or a polyurethane. For the laminated sheet, each layer of the two-or-more layers can include a same or different polymeric material than an adjacent layer of the two-or-more layers of the laminated sheet.

FIG. 3 illustrates the portal 300 having the portal barrier 304 of a splittable septum in accordance with some embodiments.

The portal barrier 304 is a split septum having a split 306 therethrough configured for establishing an optical connection, an electrical connection, or both the optical connection and the electrical connection across the septum for the one-or-more functional connections between the single-use medical device and the multiple-use medical device. When the conduit 202 of the portal 300 is formed of a flexible material (e.g., a thermoplastic such as polyethylene), opposite sides of the protruding-end portion of the portal 300 or the conduit 202 thereof can be squeezed together to open the septum for the one-or-more functional connections. Notably, the opposite sides of the protruding-end portion of the portal 300 or the conduit 202 thereof should be those at ends of the split 306 of the split septum. The polymeric material of the split septum can be a rubber such as a silicone rubber.

FIGS. 4-12 illustrate portal-establishing devices 400-1200 having different breaching mechanisms in accordance with some embodiments.

Each breaching mechanism of the portal-establishing devices 400-1200 set forth below is configured to breach the procedural barrier (e.g., the sterile barrier 18) and place the portal 200 or 300 over a breach in the procedural barrier. Notably, the breaching mechanism is oftentimes configured to breach the procedural barrier and place the portal 200 or 300 over the breach in the procedural barrier in one operation of the breaching mechanism, which operation can consist of a single motion in some embodiments. As set forth above, the portal 200 or 300 is configured to enable the one-or-more functional connections (e.g., an optical connection, an electrical connection, etc.) across the procedural barrier between the single-use medical device (e.g., the PICC 10) on the clinician-facing side of the procedural barrier and the multiple-use medical device (e.g., the relay 16, the console 24, etc.) on the patient-facing side of the procedural barrier.

Figure 4:
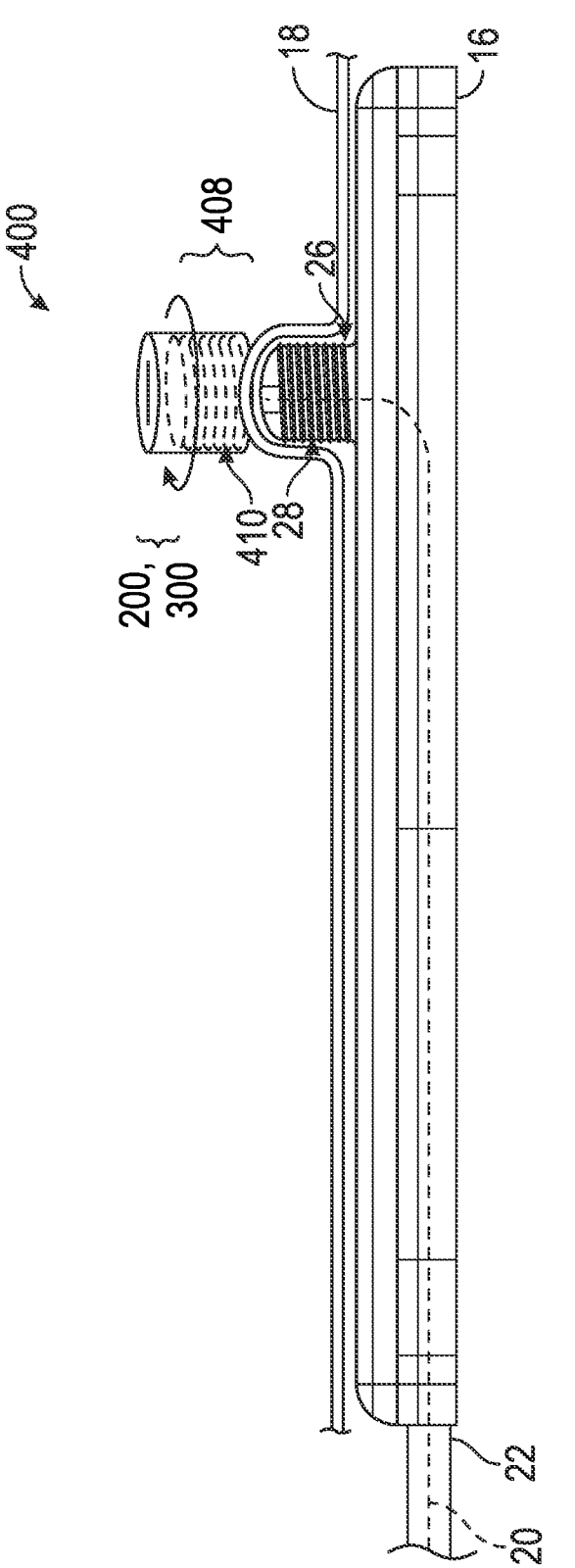
FIG. 4 illustrates a first portal-establishing device having a first breaching mechanism in accordance with some embodiments.

FIG. 4 illustrates a first portal-establishing device 400 having a first breaching mechanism in accordance with some embodiments.

As shown, the first breaching mechanism includes an extension 408 of the portal 200 or 300 having internal threads 410 configured to screw together with a protruding portion 26 of the multiple-use medical device (e.g., the relay 16) having external threads 28. The extension 408 of the portal 200 or 300 is configured to breach the procedural barrier with an internal cutting edge (e.g., a sharpened section of the internal threads 410) when screwed together with the protruding portion 26 of the multiple-use medical device with the procedural barrier therebetween.

Figure 5:
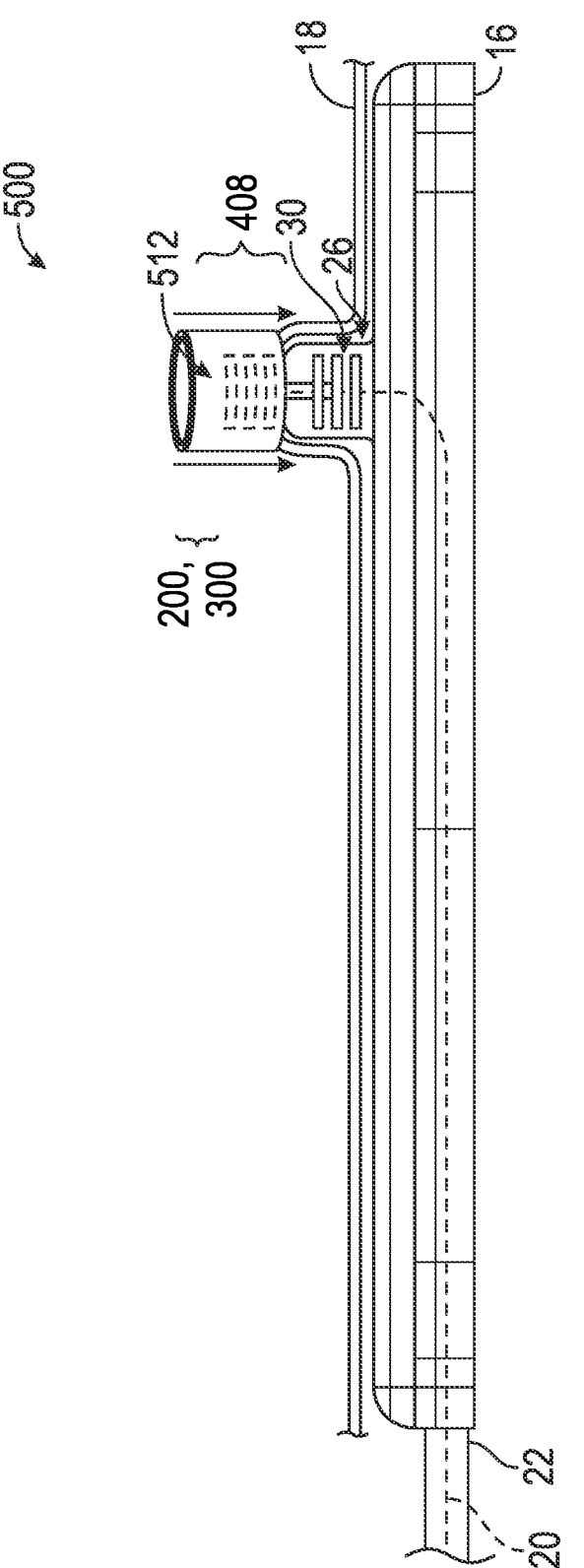
FIG. 5 illustrates a second portal-establishing device having a second breaching mechanism in accordance with some embodiments.

FIG. 5 illustrates a second portal-establishing device 500 having a second breaching mechanism in accordance with some embodiments.

As shown, the breaching mechanism includes the extension 408 of the portal 200 or 300 having one or more internal magnetic elements 512 configured to couple with one or more external magnetic elements 30 of the protruding portion 26 of the multiple-use medical device (e.g., the relay 16). The extension 408 of the portal 200 or 300 is configured to breach the procedural barrier with an internal cutting edge (not shown) when coupled together with the protruding portion 26 of the multiple-use medical device with the procedural barrier therebetween.

Figure 6:
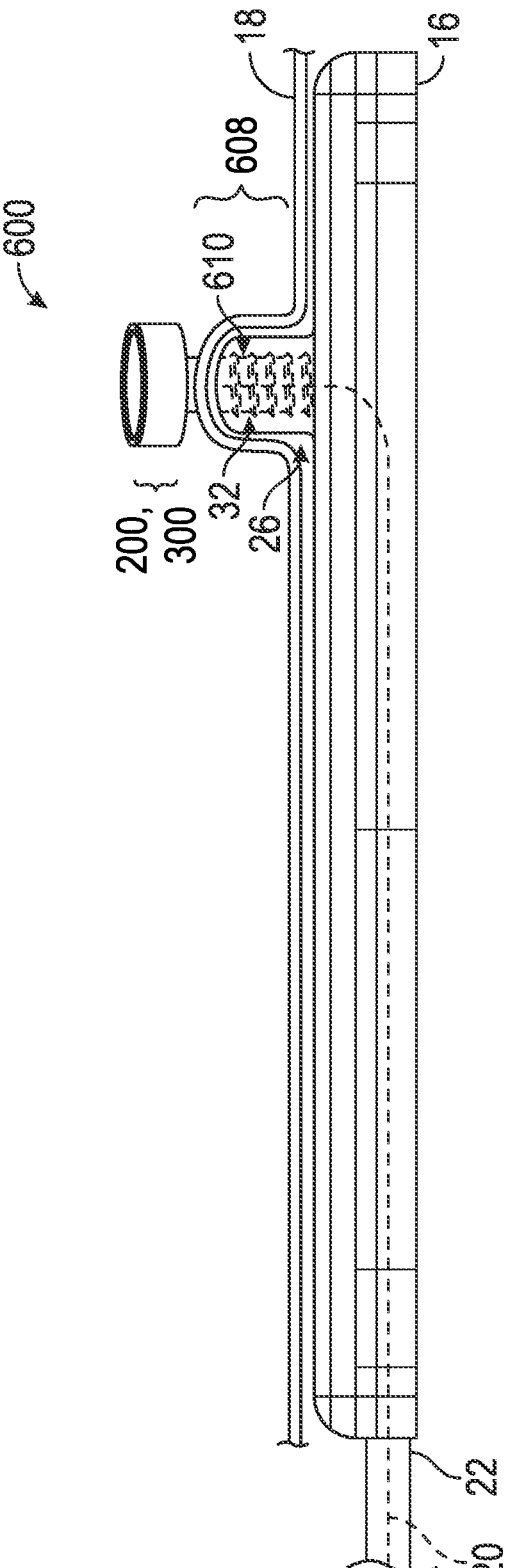
FIG. 6 illustrates a third portal-establishing device having a third breaching mechanism in accordance with some embodiments.
Figure 7:
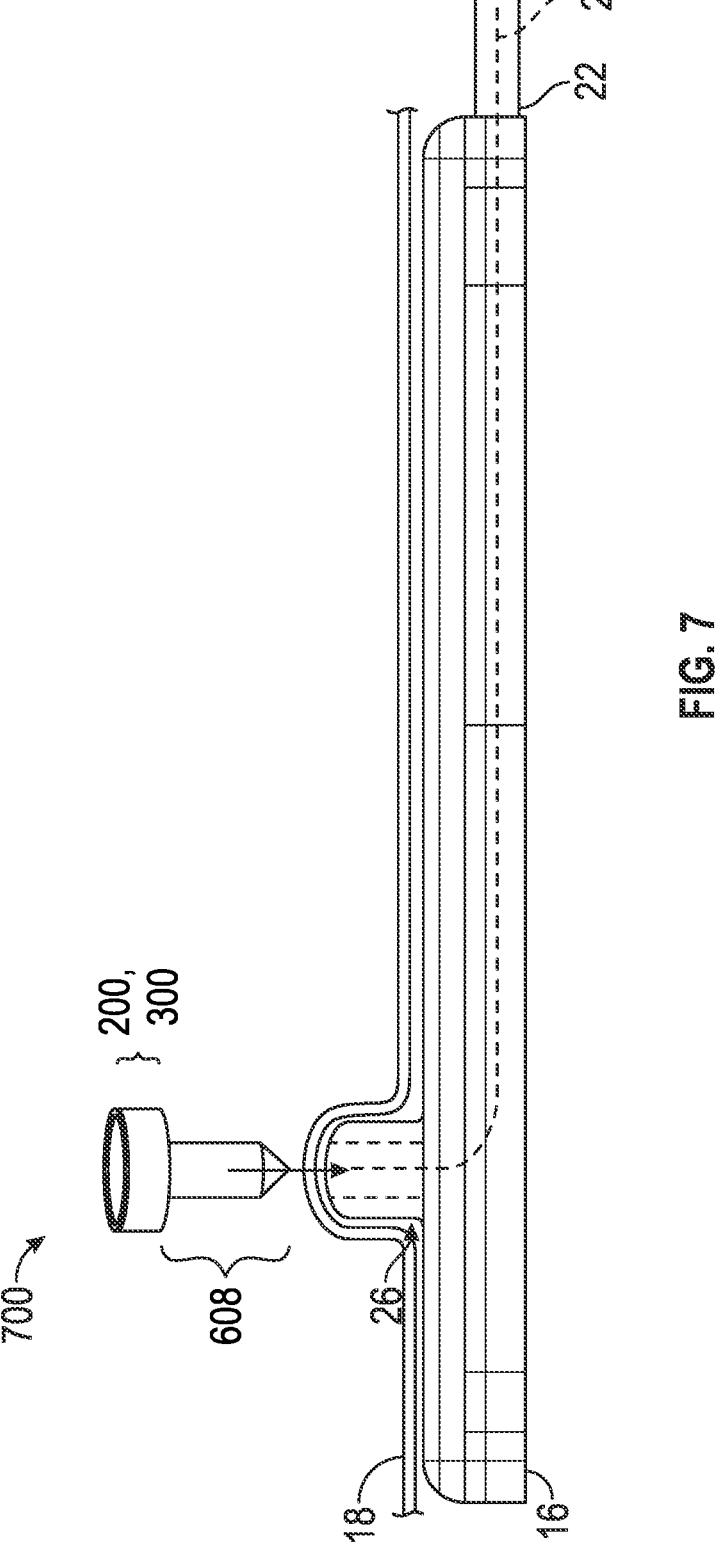
FIG. 7 illustrates a fourth portal-establishing device having a fourth breaching mechanism in accordance with some embodiments.

FIG. 6 illustrates a third portal-establishing device 600 having a third breaching mechanism in accordance with some embodiments, and FIG. 7 illustrates a fourth portal-establishing device 700 having a fourth breaching mechanism in accordance with some embodiments.

As shown in FIG. 6, the breaching mechanism includes an extension 608 of the portal 200 or 300 having external threads 610 configured to screw together with the protruding portion 26 of the multiple-use medical device (e.g., the relay 16) having internal threads 32. The extension 608 of the portal 200 or 300 is configured to breach the procedural barrier with an external cutting edge (e.g., a sharp tip of the extension 608, a sharpened section of the external threads 610, etc.) when screwed together with the protruding portion 26 of the multiple-use medical device with the procedural barrier therebetween.

As shown in FIG. 7, however, the breaching mechanism need not include the external threads 610 on the extension 608 of the portal 200 or 300. Indeed, the extension 608 of the portal 200 or 300 can be configured to breach the procedural barrier with a sharp tip of the extension 608 when inserted into the protruding portion 26 of the multiple-use medical device with the procedural barrier therebetween.

Figure 8:
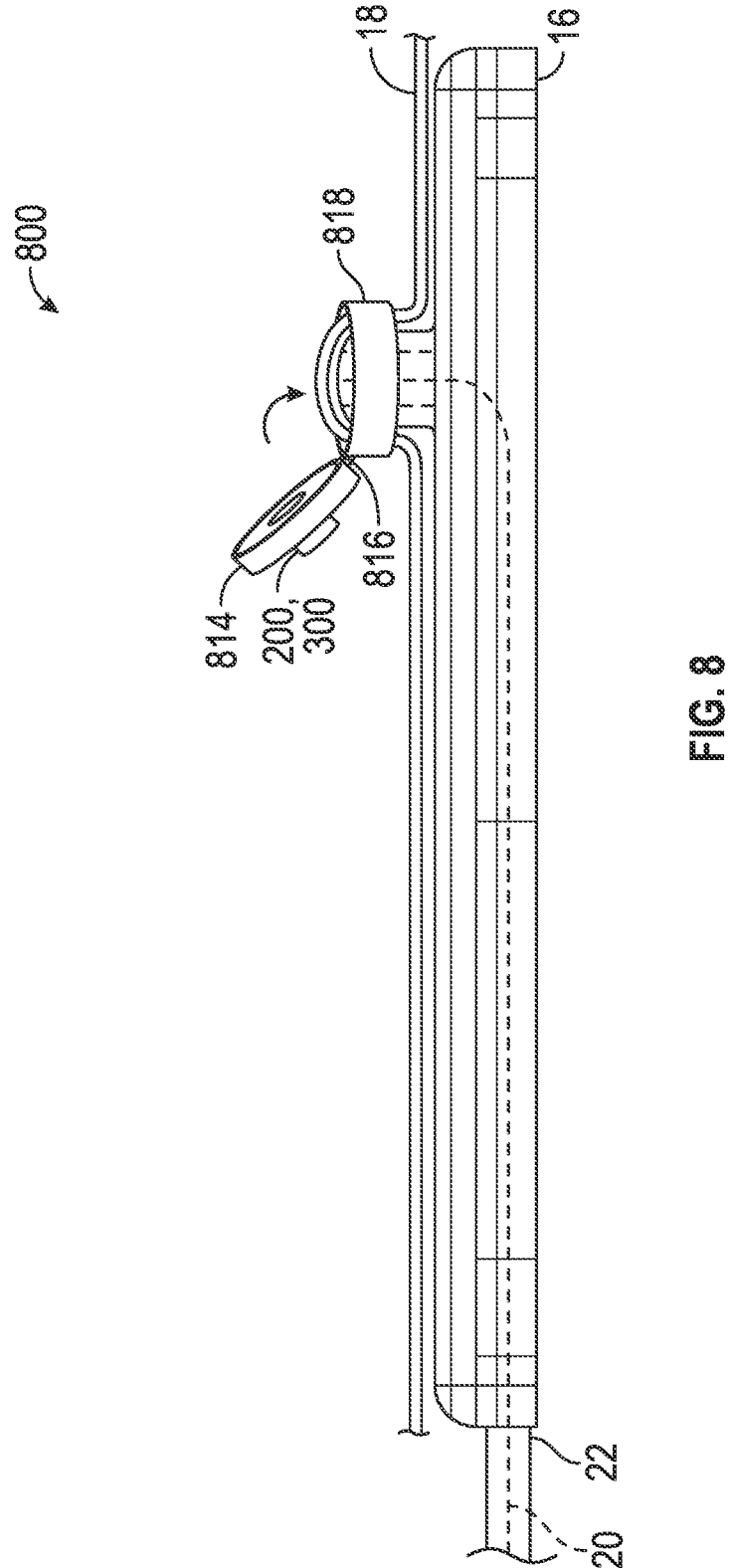
FIG. 8 illustrates a fifth portal-establishing device having a fifth breaching mechanism in accordance with some embodiments.

FIG. 8 illustrates a fifth portal-establishing device 800 having a fifth breaching mechanism in accordance with some embodiments.

As shown, the breaching mechanism includes a cap 814 coupled by a hinge pin 816 to a rigid band 818 configured to sit over the protruding portion 26 of the multiple-use medical device (e.g., the relay 16) with the procedural barrier therebetween. The cap 814 is configured to breach the procedural barrier with a cutting edge (e.g., an edge of the cap 814) when closed over the band 818. The portal extends 200 or 300 from the cap 814 along a centerline of the cap 814 such that the portal barrier 204 or 304 is aligned with the breach in the procedural barrier when the procedural barrier is breached by the cap 814.

Figure 9:
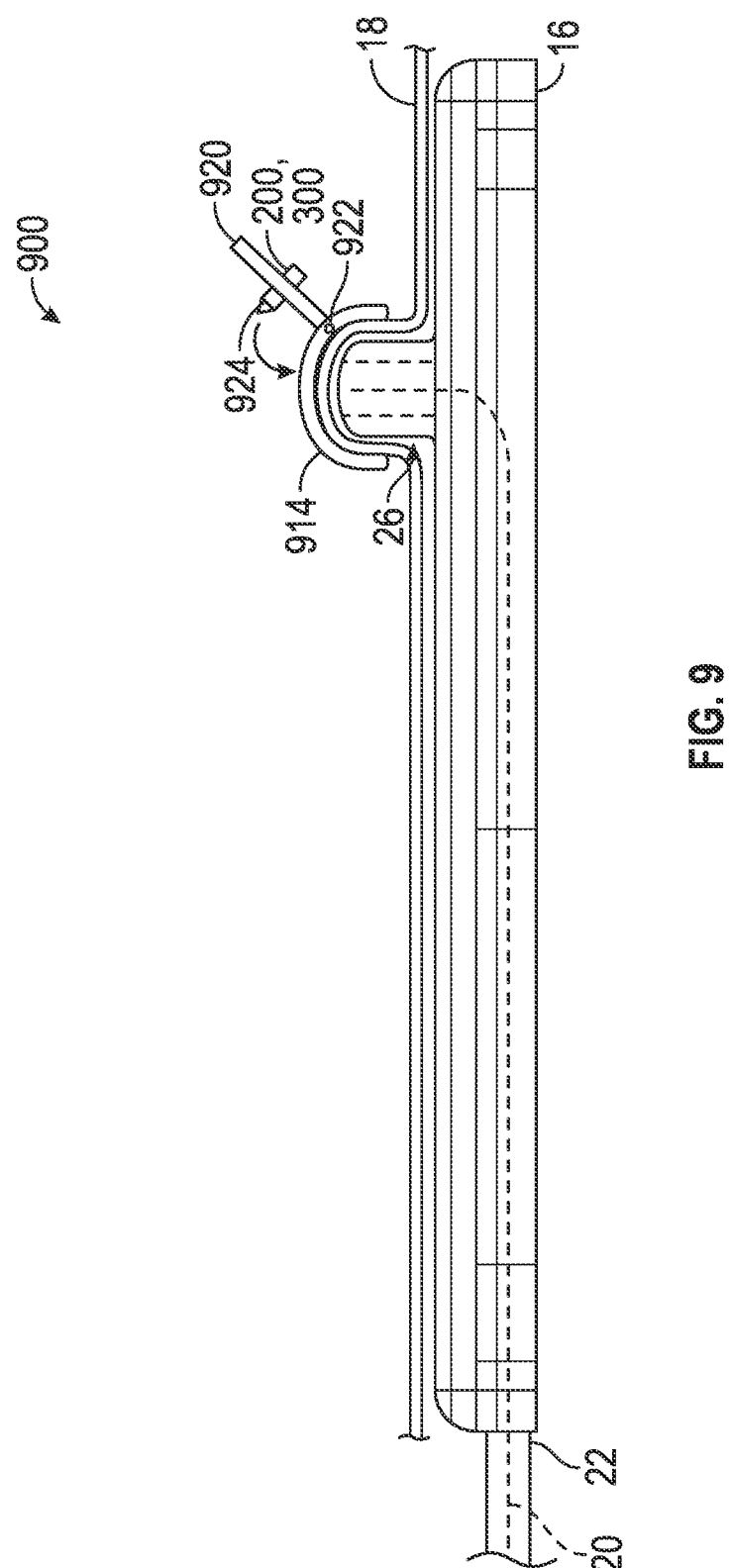
FIG. 9 illustrates a sixth portal-establishing device having a sixth breaching mechanism in accordance with some embodiments.
Figure 10:
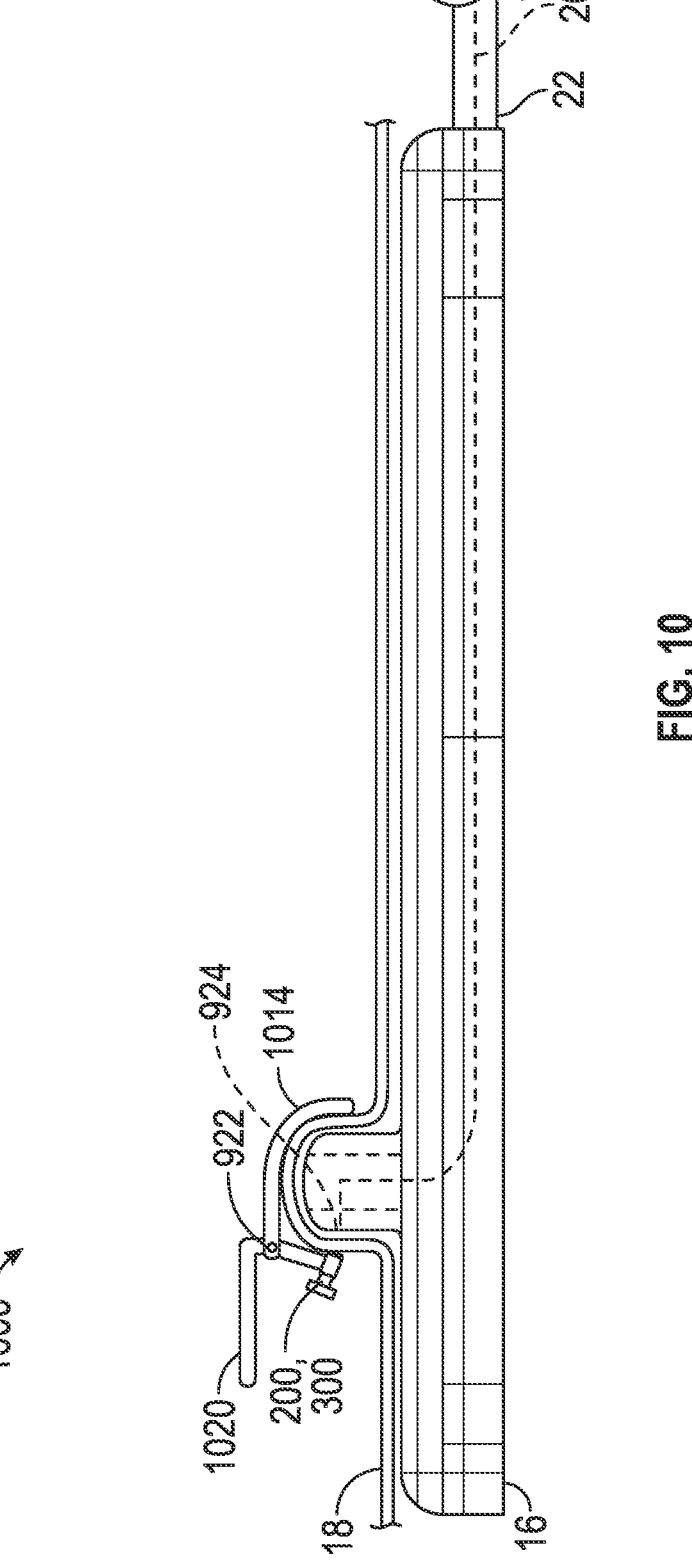
FIG. 10 illustrates a seventh portal-establishing device having a seventh breaching mechanism in accordance with some embodiments.
Figure 11:
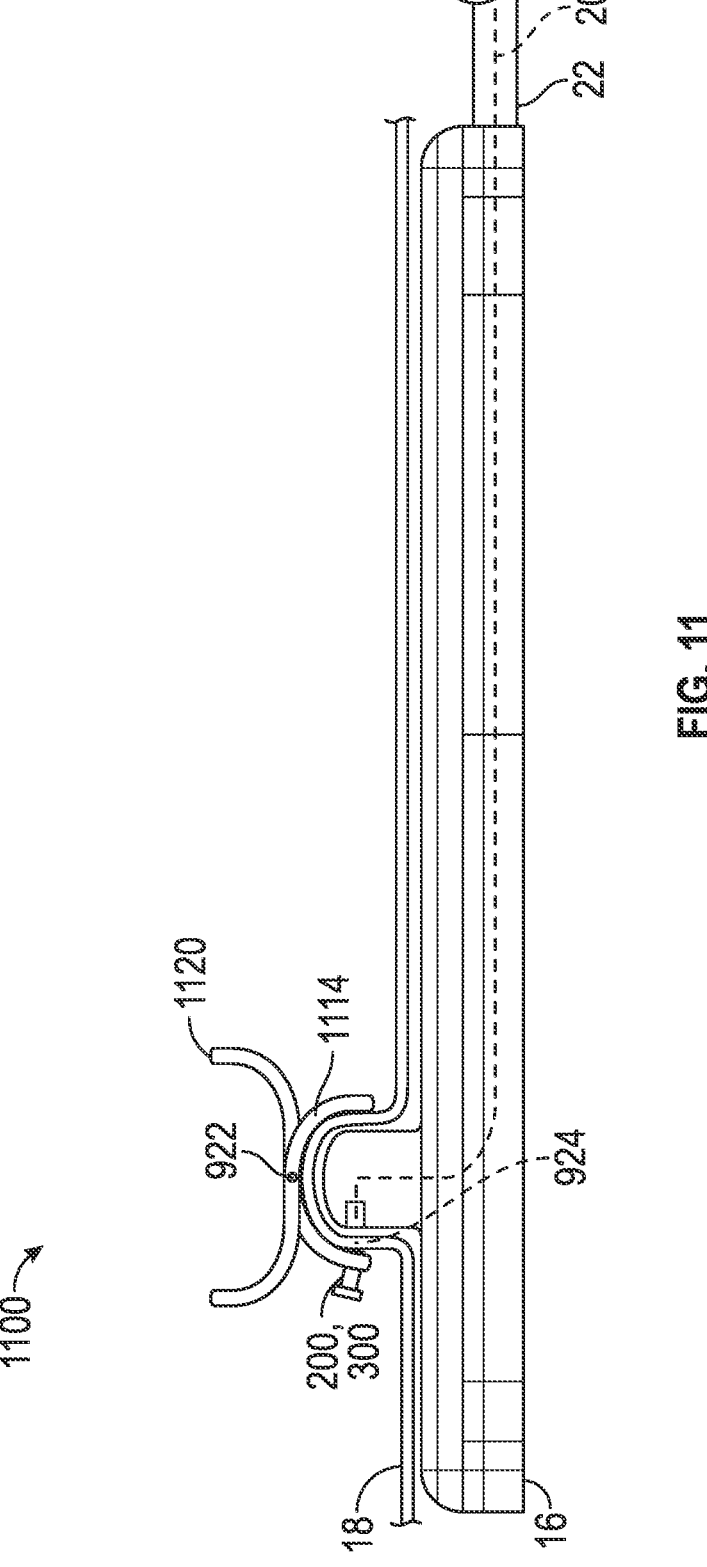
FIG. 11 illustrates an eighth portal-establishing device having an eighth breaching mechanism in accordance with some embodiments.

FIG. 9 illustrates a sixth portal-establishing device 900 having a sixth breaching mechanism in accordance with some embodiments. FIG. 10 illustrates a seventh portal-establishing 1000 device having a seventh breaching mechanism in accordance with some embodiments. FIG. 11 illustrates an eighth portal-establishing device 1100 having an eighth breaching mechanism in accordance with some embodiments.

As shown, the breaching mechanism includes a cap 914, 1014, or 1114 configured to sit over the protruding portion 26 of the multiple-use medical device (e.g., the relay 16) with the procedural barrier therebetween. An extension arm 920, 1020, or 1120 having a lever arm configured to complement a configuration of the cap 914, 1014, or 1114 is coupled by a hinge pin 922 to the cap 914, 1014, or 1114. The extension arm 920, 1020, or 1120 is configured to breach the procedural barrier with a punch 924 of the extension arm 920, 1020, or 1120 when the punch 924 is pushed through the procedural barrier by articulating the extension arm 920. The portal 200 or 300 extends from the extension arm 920, 1020, or 1120 along a centerline of the punch 924 but opposite thereof such that the portal barrier 204 or 304 is aligned with the breach in the procedural barrier when the procedural barrier is breached by the punch 924.

Figure 12:
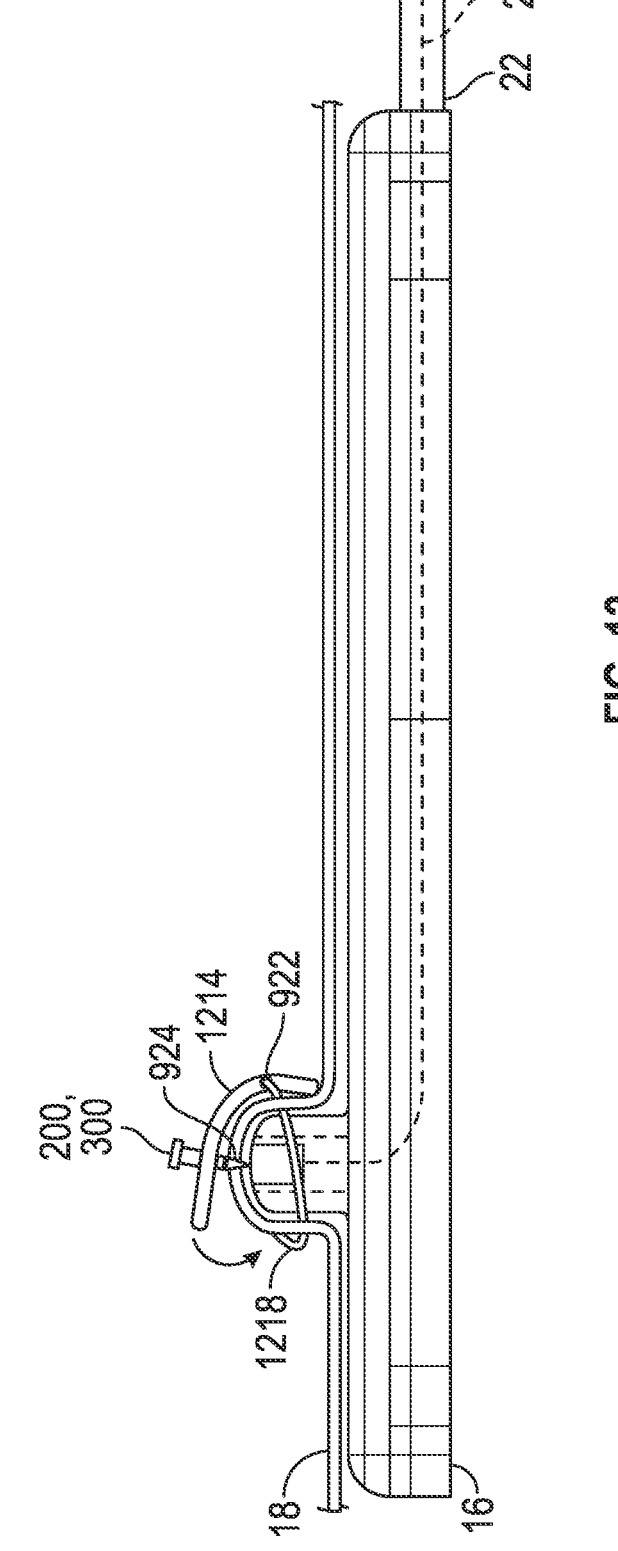
FIG. 12 illustrates a ninth portal-establishing device having a ninth breaching mechanism in accordance with some embodiments.

FIG. 12 illustrates a ninth portal-establishing device 1200 having a ninth breaching mechanism in accordance with some embodiments.

As shown, the breaching mechanism includes a rigid band 1218 configured to sit over the protruding portion 26 of the multiple-use medical device (e.g., the relay 16) with the procedural barrier therebetween. A cap 1214 coupled by the hinge pin 922 to the band 1218 is configured to breach the procedural barrier with the punch 924 of the cap 1214 when the punch 924 is pushed through the procedural barrier with by way of articulating the cap 1214. The portal 200 or 300 extends from the cap 1214 along a centerline of the punch 924 but opposite thereof such that the portal barrier 204 or 304 is aligned with the breach in the procedural barrier when the procedural barrier is breached by the punch 924.

Procedural Barriers

While not shown, a procedural barrier (e.g., the sterile barrier 18) can include the portal 200 or 300 integrated into the procedural barrier. As set forth above, the portal 200 or 300 includes the portal barrier 204 or 304 in the protruding-end portion thereof configured to enable one or more functional connections across the procedural barrier 204 or 304 between a single-use medical device on a clinician-facing side of the procedural barrier and another medical device on a patient-facing side of the procedural barrier as a multiple-use medical device (e.g., the relay 16, the console 24, etc.) on a patient-facing side of the procedural barrier.

Methods

Methods of the portal-establishing devices 400-1200 include methods of using the portal-establishing devices 400-1200. Each method of the methods of using the portal-establishing devices 400-1200 includes at least a procedural barrier-breaching step and a portal-placing step.

The procedural barrier-breaching step includes breaching a procedural barrier (e.g., the sterile barrier 18) between a single-use medical device (e.g., the PICC 10) on a clinician-facing side of the procedural barrier and another medical device such as a multiple-use medical device (e.g., the relay 16, the console 24, etc.) on a patient-facing side of the procedural barrier with a breaching mechanism of the portal-establishing device 400, 500, 600, 700, 800, 900, 1000, 1100, or 1200. Depending upon the portal-establishing device 400, 500, 600, 700, 800, 900, 1000, 1100, or 1200, the procedural barrier-breaching step includes one or more additional features or sub-steps as set forth below for each portal-establishing device of the foregoing portal-establishing devices.

The portal-placing step includes placing the portal 200 or 300 over a breach in the procedural barrier. The portal-placing step enables one or more functional connections between the single-use medical device and the multiple-use medical device through the portal 200 or 300 of the portal-establishing device 400, 500, 600, 700, 800, 900, 1000, 1100, or 1200.

FIG. 4 further illustrates a portion of the method of using the first portal-establishing device 400 in accordance with some embodiments.

As shown, the method further includes a device-mating step. The device-mating step includes screwing together the extension 408 of the portal 200 or 300 having the internal threads 410 and the protruding portion 26 of the multiple-use medical device (e.g., the relay 16) having the external threads 28. In accordance with the device-mating step, the procedural barrier-breaching step further includes breaching the procedural barrier (e.g., the sterile barrier 18) between the extension 408 of the portal 200 or 300 and the protruding portion 26 of the multiple-use medical device with the internal cutting edge of the extension 408 of the portal 200 or 300 while performing the device-mating step.

FIG. 5 further illustrates a portion of the method of using the second portal-establishing device 500 in accordance with some embodiments.

As shown, the method further includes a device-mating step. The device-mating step includes magnetically coupling together the extension 408 of the portal 200 or 300 having the one-or-more internal magnetic elements 512 and the protruding portion 26 of the multiple-use medical device (e.g., the relay 16) having the one-or-more external magnetic elements 30. In accordance with the device-mating step, the procedural barrier-breaching step further includes breaching the procedural barrier (e.g., the sterile barrier 18) between the extension 408 of the portal 200 or 300 and the protruding portion 26 of the multiple-use medical device with the internal cutting edge of the extension 408 of the portal 200 or 300 while performing the device-mating step.

FIG. 6 further illustrates a portion of the method of using the third portal-establishing device 600 in accordance with some embodiments.

As shown, the method further includes a device-mating step. The device-mating step includes screwing together the extension 608 of the portal 200 or 300 having the external threads 610 and the protruding portion 26 of the multiple-use medical device (e.g., the relay 16) having the internal threads 32. In accordance with the device-mating step, the procedural barrier-breaching step further includes breaching the procedural barrier (e.g., the sterile barrier 18) between the extension 608 of the portal 200 or 300 and the protruding portion 26 of the multiple-use medical device with the external cutting edge of the extension 608 of the portal 200 or 300 while performing the device-mating step.

FIG. 8 further illustrates a portion of the method of using the fifth portal-establishing device 800 in accordance with some embodiments.

As shown, the procedural barrier-breaching step further includes closing the cap 814 coupled by the hinge pin 816 to the rigid 818 band over the protruding portion 26 of the multiple-use medical device (e.g., the relay 16). In addition, the procedural barrier-breaching step includes breaching the procedural barrier (e.g., the sterile barrier 18) between the cap 814 and the protruding portion 26 of the multiple-use medical device with the cutting edge of the cap 814 while closing the cap 814 over the protruding portion 26 of the multiple-use medical device.

FIG. 9 further illustrates a portion of the method of using the sixth portal-establishing device 900 in accordance with some embodiments. FIG. 10 further illustrates a portion of the method of using the seventh portal-establishing 1000 device having a seventh breaching mechanism. FIG. 11 further illustrates a portion of the method of using the eighth portal-establishing device 1100 in accordance with some embodiments.

As shown, the procedural barrier-breaching step further includes articulating the extension arm 920, 1020, or 1120 coupled by the hinge pin 922 to the cap 914, 1014, or 1114 over the protruding portion 26 of the multiple-use medical device (e.g., the relay 16). In addition, the procedural barrier-breaching step includes breaching the procedural barrier (e.g., the sterile barrier 18) between the cap 914, 1014, or 1114 and the protruding portion 26 of the multiple-use medical device by pushing the punch 924 of the extension arm 920, 1020, or 1120 through the procedural barrier while articulating the extension arm 920, 1020, or 1120.

FIG. 12 further illustrates a portion of the method of using the ninth portal-establishing device 1200 in accordance with some embodiments.

As shown, the procedural barrier-breaching step further includes articulating the cap 1214 coupled by the hinge pin 922 to the rigid band 1218 over the protruding portion 26 of the multiple-use medical device (e.g., the relay 16). In addition, the procedural barrier-breaching step includes breaching the procedural barrier (e.g., the sterile barrier 18) between the cap 1214 and the protruding portion 26 of the multiple-use medical device by pushing the punch 924 of the cap 1214 through the procedural barrier while articulating the cap 1214.

Again, FIG. 2 illustrates the portal 200 having the portal barrier 204 of the transparent sheet of polymeric material in accordance with some embodiments.

The method can further include a functional connection-establishing step in view of the portal 200. The functional connection-establishing step can include establishing an optical connection for the one-or-more functional connections across the transparent sheet of polymeric material having sufficient optical transmissibility for the optical connection as the portal barrier (e.g., the portal barrier 204).

The functional connection-establishing step can additionally or alternatively include establishing an electrical connection for the one-or-more functional connections across the sheet. The sheet has sufficient tear resistance for the functional connection-establishing step when establishing the electrical connection without propagating any hole or tear made in the sheet to effectuate the electrical connection.

Again, FIG. 3 illustrates the portal 300 having the portal barrier 304 of the splittable septum in accordance with some embodiments.

The method can further include a functional connection-establishing step in view of the portal 300. The functional connection-establishing step can include establishing an optical connection, an electrical connection, or both the optical connection and the electrical connection for the one-or-more functional connections across a split septum as the portal barrier (e.g., the portal barrier 304).

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A portal-establishing device, comprising:
a portal including a portal barrier in a protruding-end portion thereof, the portal configured to enable functional connections across a procedural barrier between a single-use medical device on a clinician-facing side of the procedural barrier and a second medical device on a patient-facing side of the procedural barrier, and the portal barrier being a tear-resistant, transparent sheet of polymeric material for establishing an electrical connection thereacross for one of the functional connections between the single-use medical device and the second medical device without propagating any hole or tear made in the tear-resistant, transparent sheet to effectuate the electrical connection; and
a breaching mechanism configured to breach the procedural barrier and place the portal over a breach in the procedural barrier.

2. The portal-establishing device of claim 1, wherein the portal barrier has optical transmissibility for establishing an optical connection thereacross for another one of the functional connections between the single-use medical device and the second medical device.

3. The portal-establishing device of claim 1, wherein the breaching mechanism includes an extension of the portal having external threads configured to screw together with a protruding portion of the second medical device having internal threads, the extension of the portal configured to breach the procedural barrier with an external cutting edge when screwed together with the protruding portion of the second medical device with the procedural barrier therebetween.

4. The portal-establishing device of claim 1, wherein the portal-establishing device is sterile and the procedural barrier is a sterile drape.

5. The portal-establishing device of claim 1, wherein the breaching mechanism includes an extension of the portal having internal threads configured to screw together with a protruding portion of the second medical device having external threads, the extension of the portal configured to breach the procedural barrier with an internal cutting edge when screwed together with the protruding portion of the second medical device with the procedural barrier therebetween.

6. The portal-establishing device of claim 1, wherein the breaching mechanism includes an extension of the portal having one or more internal magnetic elements configured to couple with one or more external magnetic elements of a protruding portion of the second medical device, the extension of the portal configured to breach the procedural barrier with an internal cutting edge when coupled together with the protruding portion of the second medical device with the procedural barrier therebetween.

7. The portal-establishing device of claim 1, wherein the breaching mechanism includes an extension of the portal having a sharp tip configured to breach the procedural barrier when inserted into a protruding portion of the second medical device with the procedural barrier therebetween.

8. A method of a portal-establishing device, comprising:
breaching a procedural barrier between a single-use medical device on a clinician-facing side of the procedural barrier and a second medical device on a patient-facing side of the procedural barrier with a breaching mechanism of the portal-establishing device; and
placing a portal over a breach in the procedural barrier, the portal including a portal barrier in a protruding-end portion thereof, the portal barrier being a tear-resistant, transparent sheet of polymeric material for establishing an electrical connection thereacross between the single-use medical device and the second medical device without propagating any hole or tear made in the tear-resistant, transparent sheet to effectuate the electrical connection, thereby enabling a functional connection between the single-use medical device and the second medical device through the portal of the portal-establishing device.

9. The method of claim 8, further comprising establishing an optical connection for a second functional connection across the tear-resistant, transparent sheet of polymeric material, the portal barrier having optical transmissibility for the optical connection.

10. The method of claim 8, further comprising:

screwing together an extension of the portal having internal threads and a protruding portion of the second medical device having external threads; and breaching the procedural barrier between the extension of the portal and the protruding portion of the second medical device with an internal cutting edge of the extension of the portal while screwing together the extension of the portal and the protruding portion of the second medical device.

11. The method of claim 8, further comprising:

magnetically coupling together an extension of the portal having one or more internal magnetic elements and a protruding portion of the second medical device having one or more external magnetic elements; and breaching the procedural barrier between the extension of the portal and the protruding portion of the second medical device with an internal cutting edge of the extension of the portal while magnetically coupling together the extension of the portal and the protruding portion of the second medical device.

12. The method of claim 8, further comprising:

screwing together an extension of the portal having external threads and a protruding portion of the second medical device having internal threads; and breaching the procedural barrier between the extension of the portal and the protruding portion of the second medical device with an external cutting edge of the extension of the portal while screwing together the extension of the portal and the protruding portion of the second medical device.

13. The method of claim 8, wherein the portal-establishing device is sterile and the procedural barrier is a sterile drape.

14. A procedural barrier, comprising:

a portal integrated into the procedural barrier, the portal including a portal barrier in a protruding-end portion thereof configured to enable functional connections across the procedural barrier between a single-use medical device on a clinician-facing side of the procedural barrier and a second medical device on a patient-facing side of the procedural barrier, and the portal barrier being a tear-resistant, transparent sheet of polymeric material for establishing an electrical connection thereacross for one of the functional connections between the single-use medical device and the second medical device without propagating any hole or tear made in the tear-resistant transparent sheet to effectuate the electrical connection.

* * * * *